United States Patent [19]

Meltzer

[11] Patent Number: 5,306,510
[45] Date of Patent: *Apr. 26, 1994

[54] AUTOMATED PIPETTING SYSTEM

[75] Inventor: Walter Meltzer, New Milford, Conn.

[73] Assignee: Cyberlab, Inc., Norwalk, Conn.

[ * ] Notice: The portion of the term of this patent subsequent to Oct. 8, 2008 has been disclaimed.

[21] Appl. No.: 649,710

[22] Filed: Feb. 1, 1991

Related U.S. Application Data

[63] Continuation-in-part of Ser. No. 144,576, Jan. 14, 1988, Pat. No. 5,055,263.

[51] Int. Cl.$^5$ .............................................. B01L 3/02
[52] U.S. Cl. .................................. 422/65; 73/864.24;
73/864.25; 422/63; 422/81; 422/99; 422/100;
422/104; 436/180; 436/809
[58] Field of Search .................. 422/65, 99, 63, 100,
422/67, 104, 68, 81; 436/180, 809; 73/864.25,
864.14, 864.17, 863.32, 864.24

[56] References Cited

U.S. PATENT DOCUMENTS 5,055,263 10/1991 Meltzer .................................. 422/65

Primary Examiner—Lynn M. Kummert
Assistant Examiner—Amalia Santiago
Attorney, Agent, or Firm—Michael Marinangeli

[57] ABSTRACT

An improved automated pipetting system for programmingly pipetting predetermined quantities of liquid between preselected groups of test tubes, vials or wells arranged on a horizontal table. A substantially rigid overhead frame mounted over the table on which the test tube arrays or the like are arranged. A pair of parallel X-axis guide shafts mounted in the rigid frame. A pair of helical screws rotatably mounted in the frame parallel to the pair of X-axis guide shafts. Each helical screw is driven by a stepper motor coaxially connected thereto. A pair of X-axis roller sections are movably mounted on the pair of X-axis guide shafts and support a Z-axis probe mechanism via a pair of Y-axis guide shafts and a parallel Y-axis helical screw. A stepper motor is drivingly and coaxially connected to the Y-axis screw for moving the Z-axis probe mechanism along the Y-axis guide shafts. The Z-axis probe mechanism is movably mounted on the pair of Y-axis guide shafts. The Z-axis probe mechanism is also connected to at least one stepper motor for moving a corresponding probe along the Z-axis. The Z-axis probe mechanism may include a plurality of probes, each one of which is drivingly connected to a stepper motor. The movement of the stepper motors are controlled by a computer in accordance with a computer program.

20 Claims, 12 Drawing Sheets

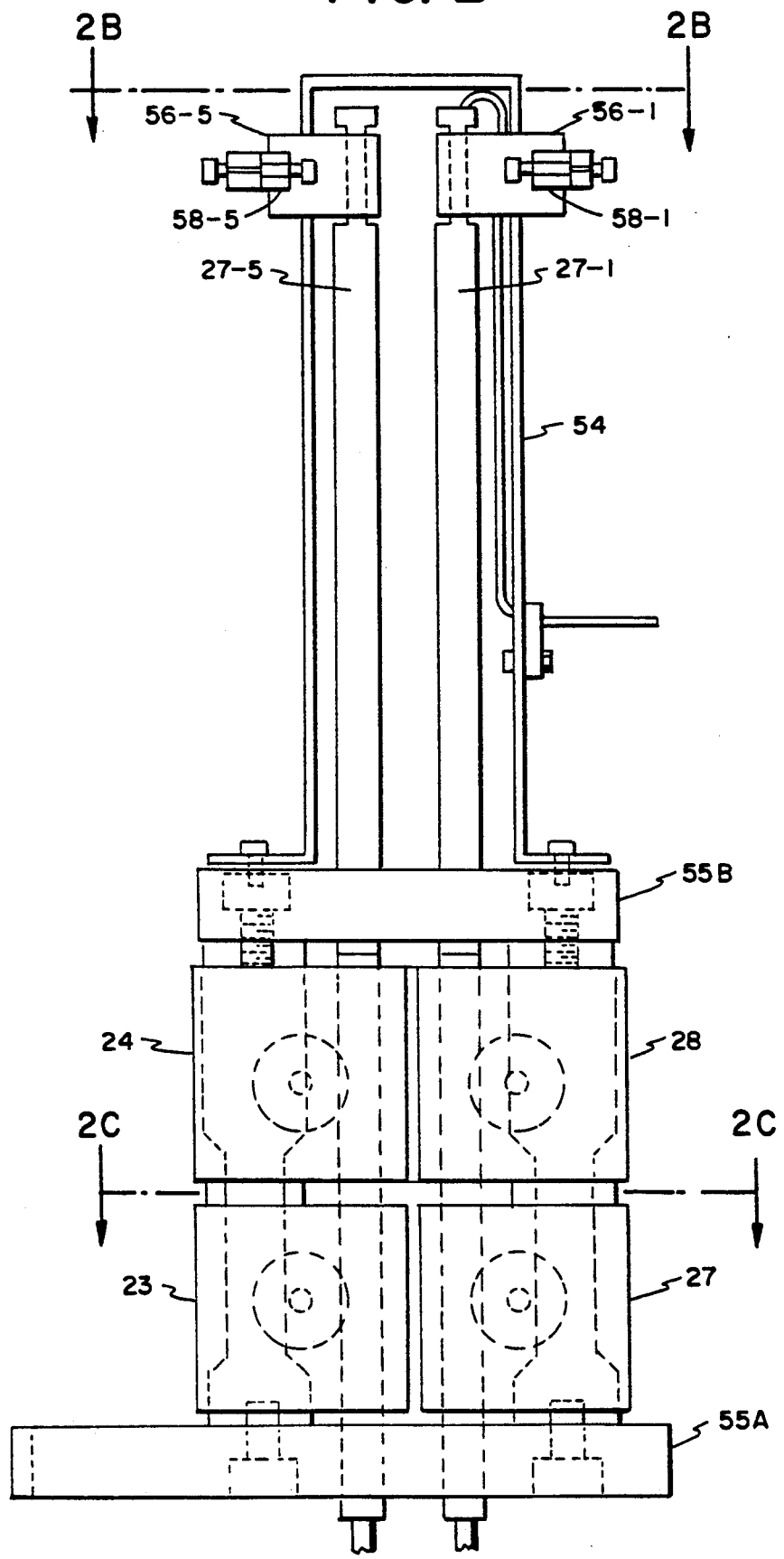

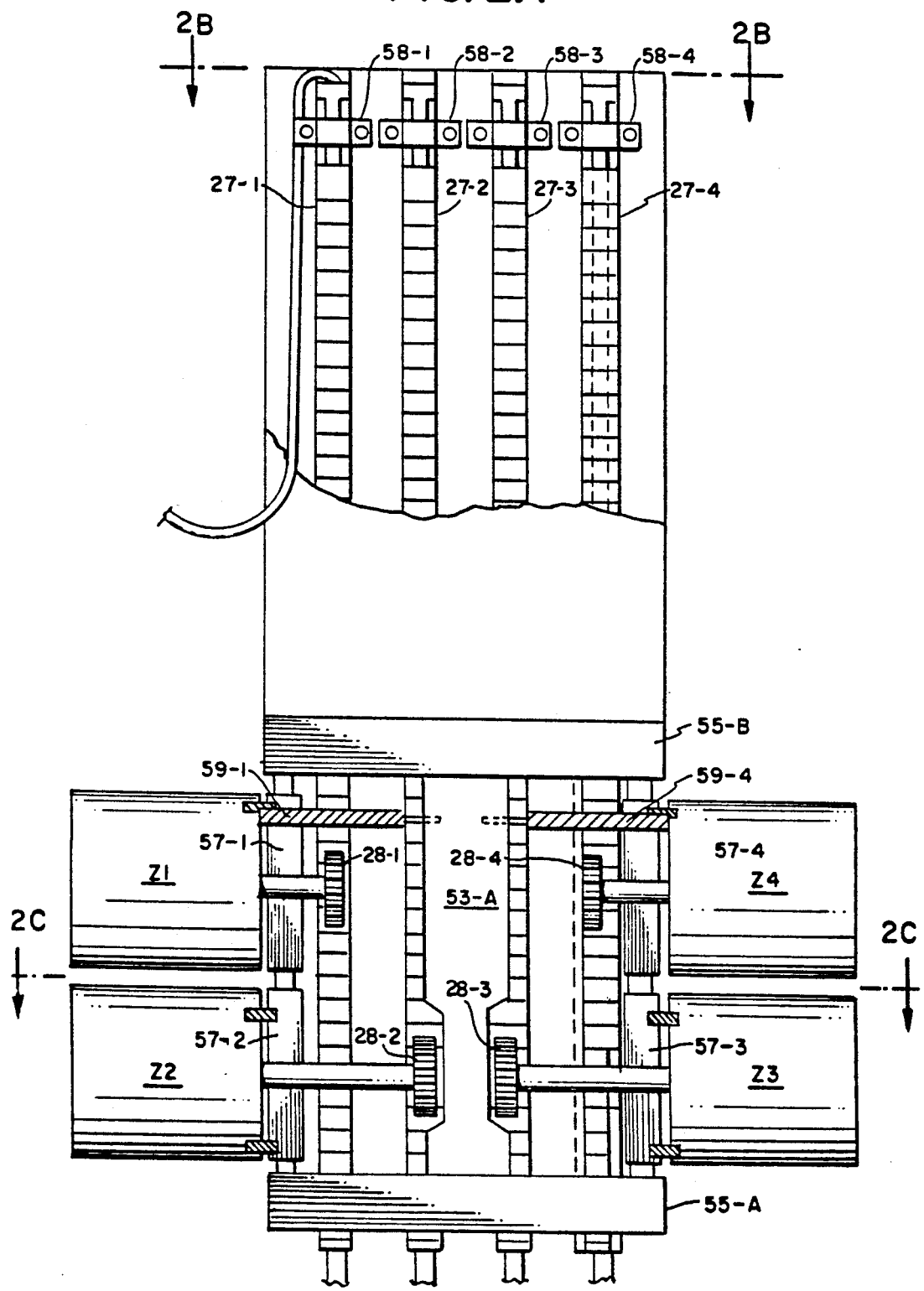

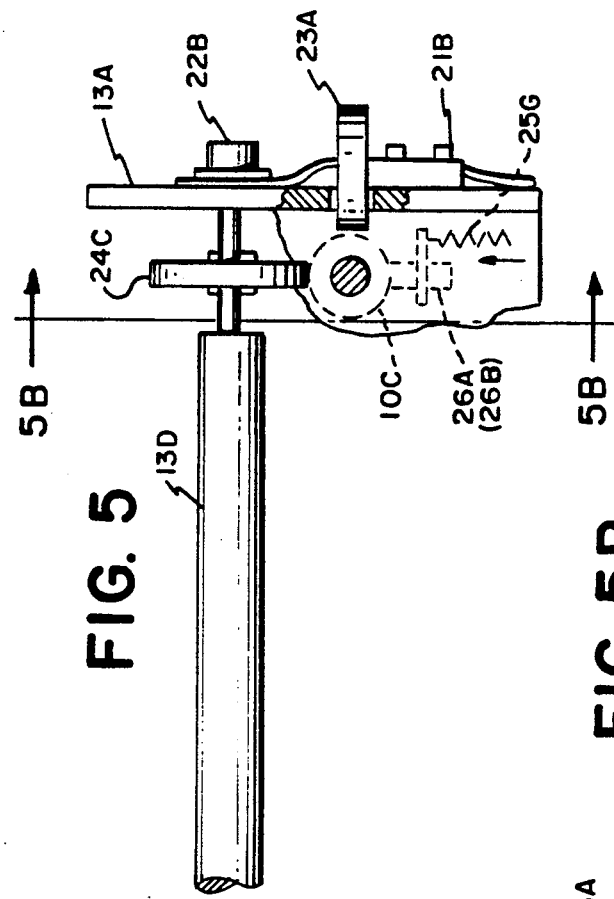
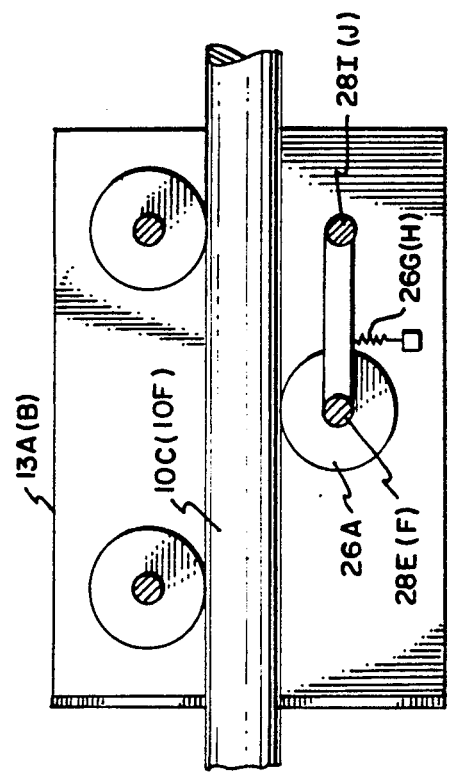
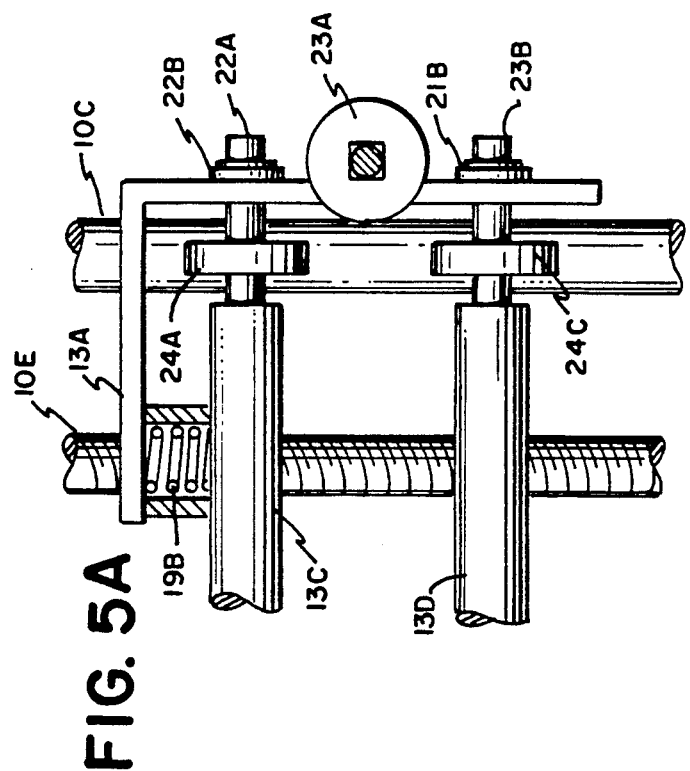

FIG. 6
FIG. 7
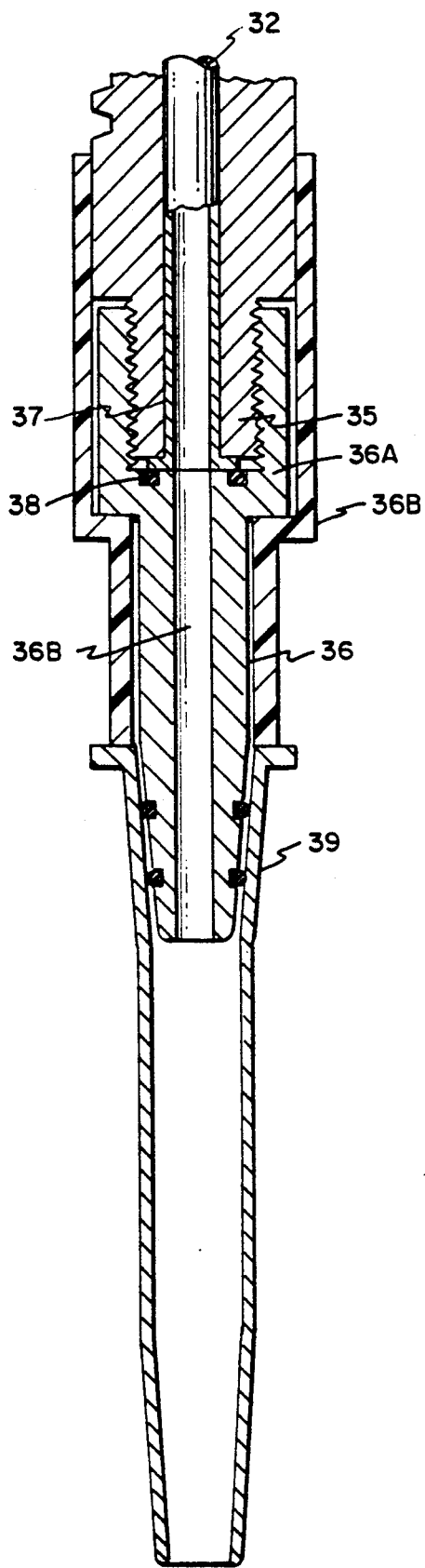
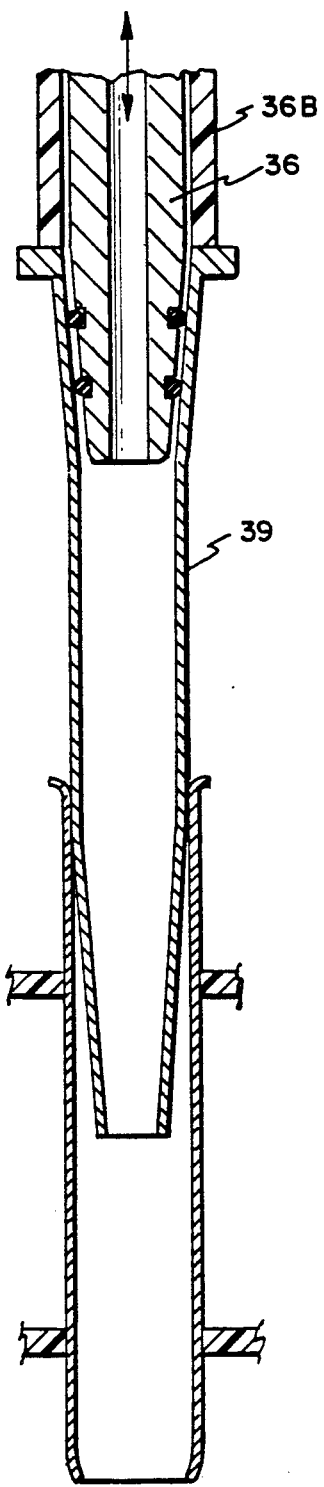

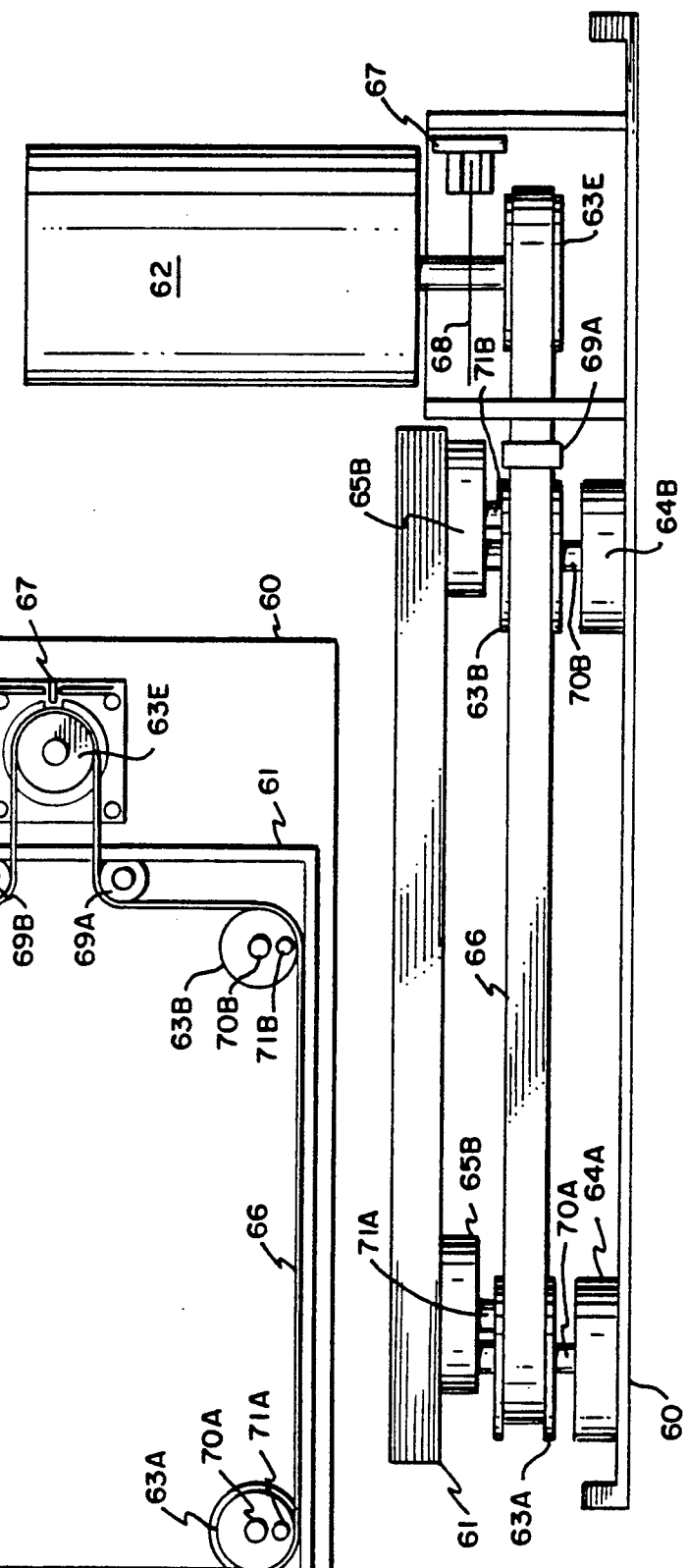

AUTOMATED PIPETTING SYSTEM

CROSS-REFERENCE TO RELATED APPLICATION

This application is a continuation-in-part of Applicant's application, Ser. No. 144,576, filed Jan. 14, 1988, now U.S. Pat. No. 5,055,263 issued Oct. 8, 1991, and entitled "AUTOMATED PIPETTING SYSTEM."

BACKGROUND OF THE INVENTION

This invention relates to certain improvements in an automated pipetting system and, particularly, to an improved system with multiple pipetting probes which have individual positioning and individual metering controls.

Conventional automated pipetting systems are used to perform repetitive laboratory mixing, sampling or transferring of fluids in multiwell plates or multiple sets of vials or test tubes. Generally, one or more probes having fluid carrying tips are manipulated over an array of tubes by an arm which is robotically driven in three dimensions (X, Y, Z axes) to carry out programmed procedures under control of an associated computer. Desired procedures include dropping measured quantities of fluids into the tubes at specified depths, prewetting the probes' tips, blowing out the tips to clear them, touching the tips to samples or a cleaning surface and changing the tips.

However, conventional pipetting systems have a number of limitations. Many systems have only one probe with one tip. Some systems have changeable pipette heads with multiple tips in parallel, but all tips are controlled together so that each one dispense the same amount as the others. A few systems have independently metered probes, but they are not independently driven in the Z-axis (vertical) direction because the space taken up by the probe drive mechanisms would not fit the desired tight spacing of the plate wells of test tube array. Therefore, such systems can only drive all the probe tips together to the same depth in the wells or tubes. There are some systems with independent Z-axis drive for up to four probes, but the manner in which they are driven and supported preclude the possibility of automatically picking up and ejecting disposable tips or adding more probes. Because of the design of the supporting arm is typically only supported from the rear the precision to which the probes can be positioned in the Z-axis is compromised. None have an integral mixing table.

SUMMARY OF THE INVENTION

The entire design of this device is devoted to producing a high precision, rapid throughput unit at a cost lower than previously attainable. The accuracy of this unit (0.005 inches on all axes) is essential to attaining highly reproducible pipetting results. The importance of lower cost cannot be underestimated because it makes a sophisticated automated machine available to the small lab and solo researcher. It is as important as the advent of the home computer was to the computer industry. There are two trains of thought when designing a high precision device. The first is to machine every part to high tolerance. The second is to design a stable structure (such as a welded steel subframe) and incorporate mechanisms with a very low wear rate (such as ball bearings rolling on hardened guide rails) with parts designed to achieve high machine tolerance at low cost (it is easier to achieve concentricity on a lathe than locate a hole precisely on a milling machine) and make a one time alignment using shims or adjustments. This design has accomplished that providing more features, greater versatility, equal or better precision and at half the cost of competitive units.

A unique feature of the automated pipetting system of this invention is the removability of the Z-axis probe assembly. While this may appear to be a simple concept, at first glance, it has been found, in practice, to be quite difficult to incorporate into design and has not been satisfactorily achieved by any competing models. The importance of a modular type system cannot be over-emphasized. Again, by analogy to a personal computer, it can be compared to plug-in boards or other exchangeable parts. This feature offers important advantages to both the end user and the manufacturer and makes for a much more attractive product.

Some of the main advantages for the manufacturer of the automated pipetting system of this invention are: (1) It permits the manufacture of only one transport model to be used with a variety of Z-axis probe assemblies, thus reducing inventory and manufacturing costs. (2) The Z-axis probe assembly can be changed from a simple dispenser unit with a choice of one to eight fixed probes (or manifolds) to an eight probe unit independently driven Z-axis motor by means of a simple change of Z-axis assembly and power supply/drive unit. Both can be changed by the end user in a few minutes. (3) Special Z-axis design units can be easily installed without a re-design of the base unit. For example, a pH measuring probe can be attached to a Z-axis drive and create a machine that automatically measures the pH of a rack of test tubes. (4) Improvements or updates can be done on an assembly basis, without obsoleting old stock.

Some of the main advantages for the end user of the automated pipetting system of this invention are: (1) The user's investment is protected. The user can purchase upgrades on a modular basis. (2) It is not necessary to purchase the most expensive model initially. A two channel Z-axis model might suffice for the first year, and as needs increase or funds become available, an upgrade would cost substantially less than a new unit. (3) If a special function application is needed, only a new Z-axis module need be purchased, and the automated pipetting system of this invention serves a dual purpose. (4) Service of the new automated pipetting system of this invention is much easier. The most likely place where a malfunction may occur is in the Z-axis assembly or the power supply/drive unit. Both of these units are easily detachable and shippable in the improved design of the present invention.

The constructional details of the removable units are as follows. The Z-axis assembly is held in place by four locator pins. Tubing is held in place by clip on connectors, and there is one 50 pin D-subminiature connector supplying power. The power supply unit is secured by simply setting the four locator pins into the four receptacles. Gravity is sufficient for retainment. As the number of probes are increased, more pumps would be needed. These have slip-on connections to the left support arm and are described elsewhere.

It is, therefore, a principal object of the invention to provide an automated pipetting system having a plurality of independently driven and dispensing probes which fit the tight spacing for multiwell plates and test tube arrays. It is another object of this invention to provide a pipetting system in which each probe can be positioned, particularly in the Z-axis direction, with a high degree of precision and controlled to handle a quantity of fluid as small as one microliter accurately.

A further object of the invention is to provide a pipetting system which can automatically pick up and eject disposable pipette tips.

Still another object of the invention is to provide a pipetting system with a means for mixing reagents at controlled intervals and durations.

It is a further object of the invention to provide a carriage moving mechanism which is very rugged and stable.

In accordance with the above-described objects, the automated pipetting system of the invention has a rigid overhead frame above a table for supporting the test tube or multiwell arrays, a pair of X-axis guide shafts spaced apart in parallel on two opposite sides of the frame, a pair of X-axis helical screw shafts each disposed in parallel with a respective X-axis guide shaft, a subframe driven in the X-axis direction by the X-axis screw shafts by means of a pair of stepper motors which are respectively connected to the screw shafts; the subframe has rollers at its opposite ends which are mounted on roller bearings which roll on the X-axis guide shafts in a horizontal direction; a pair of Y-axis guide shafts supported on the subframe in parallel with each other; one Y-axis helical screw shaft in between the two Y-axis guide shafts; a carriage driven via a stepper motor in the Y-axis direction by the Y-axis screw shaft; the carriage is supported by roller bearings and rollers which roll on the Y-axis guide shafts; at least one row of probes, having separate drive mechanisms for independent Z-axis travel (vertical) movement are mounted on the carriage. The drive mechanisms for the Z-axis are stacked vertically one above each other on each side of the row of probes, and each mechanism, preferably a stepper motor, controls a respective probe via an output shaft of a given length extending from the drive mechanism to the row position of the respective probes.

In the aforedescribed construction, the frame, the X and Y-axis screw shafts and guide shafts allow for precise positioning of the carriage in the X and Y directions. The subframe and the carriage each have rollers rolling on top surfaces of the corresponding guide shafts and spring biased positioning rollers oriented perpendicular to the translation rollers for maintaining the moving part in precise alignment with the guide shafts. The stacked arrangement of the probe drive mechanisms along the Z-axis allows four or more probes (eight probes are illustrated in the drawing) to be positioned close together in a row according to the tight spacing of the multiwell or test tube array. Two or more such rows (two rows are illustrated in the drawings) of independently driven probes may be used.

In the preferred embodiment of the invention, eight probes are arranged in two rows of four each. The probes are fixed on the ends of linear racks, each of which is independently driven by means of a rack and pinion gear on the output shaft of the respective drive mechanism (stepper motor). Three of the four probes are preferably connected to external syringe pumps via tubing that passes through a hole bored in the Z-axis racks and exits from the side of the transport. Similarly, the other probes in each row are preferably connected to one channel each of a peristaltic pump. The syringe pumps draw small to moderate quantities of fluid (1-5000 $\mu$l) into the disposable pipette tips. The peristaltic pump draws larger quantities of fluid (up to 5 liters/hour) continuously through the two non-disposable probe tips and connecting tubing. The syringe pumps are preferably external units consisting of two syringes each and having preferably five different sizes (10 $\mu$l, 100 $\mu$l, 1 ml, 5 ml and 10 ml). The syringe pumps are preferably of the standard glass barrel syringe type with a teflon piston. The peristaltic pump is also arranged as an external unit. It is of the two channel, 15 roller design type, with rigidly adjusted shoes and is directly driven by a stepper motor. The syringe pumps are preferably also stepper motor driven via a fine pitched helix screw. Different combinations of pumps of different manufacture may be used, since all eight probes are identical in construction. Interchangeable tip holders of improved double o-ring design are screwed into the bottom of the Z-axis racks and can precisely pickup or discharge disposable pipette tips via downward or upward motion of the linear racks. This ejection method of disposable pipette tips will be described in further detail.

Any numerical combination of peristaltic and syringe pumps, or pumps of different manufacture, may be used. The probes have interchangeable tip holders which can pickup or discharge different size disposable pipette tips.

The helical screw shafts of the X-Y positioning frame are driven by stepper motors, and micro switches are provided to mark the home position of the carriage. When new tip holders are initially installed, the computer does an automatic Z-axis calibration on request. It does this by picking up new disposable tips of each respective size and then moving each probe to the maximum downward position in one tube of each different type of test tube rack or microwell. The computer marks in memory how many steps it took to move each respective probe from the bottom of each type of rack, as well as each type of disposable tip rack, to the point where it first interrupts a photocell limit switch. Thereafter, upon picking up a new disposable tip, the computer checks the number of steps needed to pick up a new tip against the respective calibration number. If they are not within a prescribed limit indicating that the tip box was empty, or the tip failed to seat all the way on the tip holder, an appropriate warning message is issued by the computer, and execution is paused until corrected manually. The calibration factors representing the distance between the test tube or microwell rack bottoms are used so that the probes can be accurately stepped to the proper depth for the amount of liquid present. Each time a probe finishes a pipetting action, it moves to a point 10 steps past the limit switch detection point. As the computer causes the probe to move downward, it starts counting only as the point of detection is passed.

BRIEF DESCRIPTION OF THE DRAWINGS

The above objects, features and advantages of the invention are described in greater detail below, in conjunction with the drawings, of which:

FIG. 2 is an elevational front view, partially in cross-section, of the removable Z-axis assembly unit;

FIG. 2a is a side elevational view of the Z-axis assembly unit, shown partially in cross-section.

FIG. 5 is a schematic side elevational view of the roller section of the X-axis moving mechanism for the system of FIG. 1;

FIG. 5a is a plan schematic view of the other roller section of the X-axis moving mechanism;

FIG. 5b is a schematic side elevational cross-sectional view taken along plane 5b—5b of FIG. 5;

FIG. 6 is a side sectional view of a tip holder with changeable tip shown in a first operative position;

FIG. 7 is a side sectional view of the tip holder with a changeable tip for the probe shown in a second operative position;

FIG. 11 is a plan view showing the constructional details of the vortexing (mixing) table;

FIG. 11a is a front elevational view along plane 11a–11a of FIG. 11 of the vortexing table;

DETAILED DESCRIPTION OF THE DRAWINGS

Figure 1:
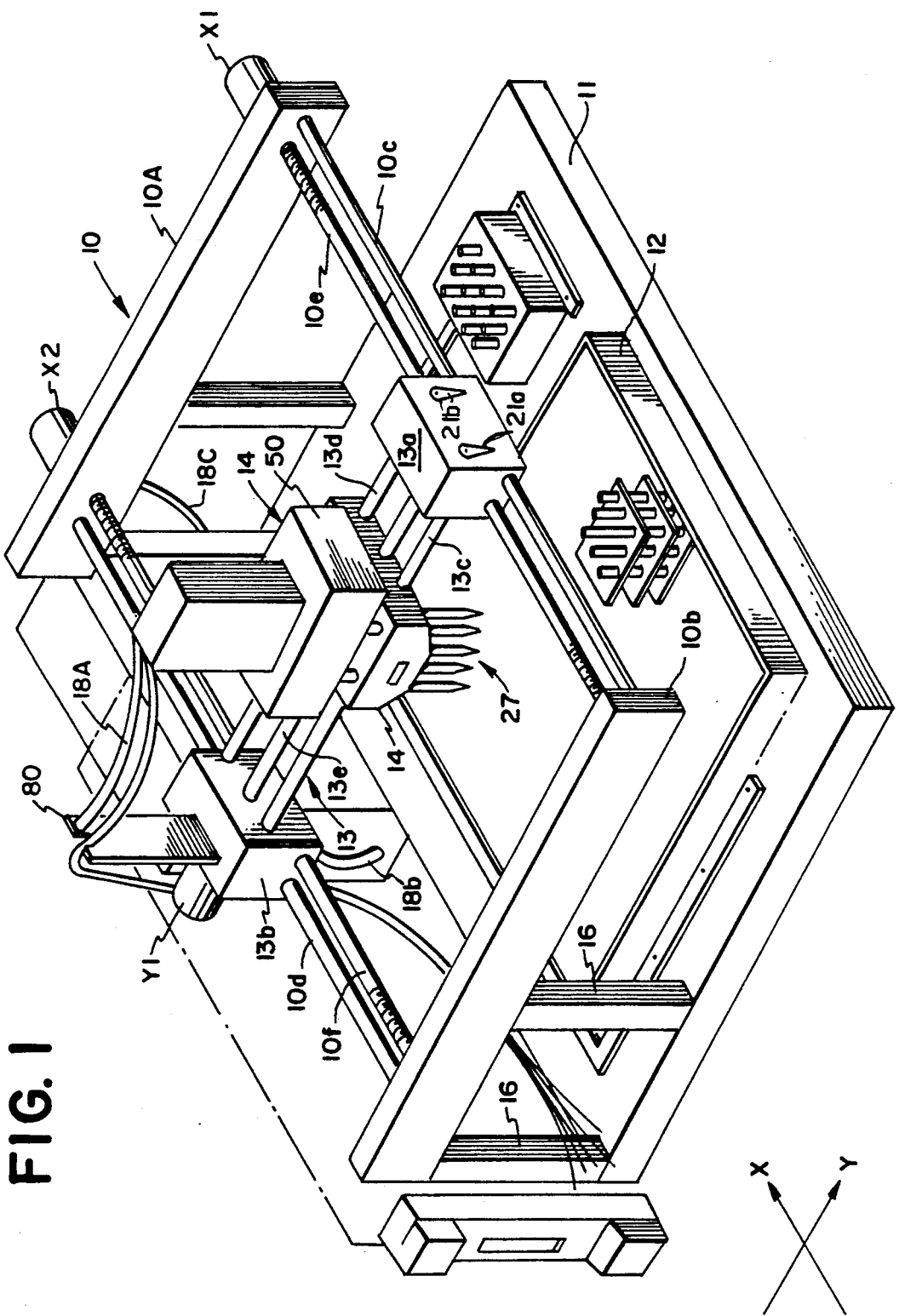
FIG. 1 is a perspective view of an automated pipetting system in accordance with the invention.

Referring to FIG. 1, an automated pipetting system, in accordance with the invention, has an overhead frame assembly, indicated generally by reference numeral 10, having frame sides 10a and 10b, subframe assembly 13 supported on roller sections 13a and 13b on guide shafts 10c and 10d of frame 10 for movement in the X-axis direction and carriage 14 supported on guide shafts 13c and 13d of subframe 13 for movement in the Y-axis direction. Base 11 supports tray or locator plate 12 for holding multiwell plates or test tube arrays on which the pipetting procedures are performed. Water bath tray 12 sits on top of base 11, so that the test tube arrays are located within the X-Y axes range of movement under carriage 14. The tray has locator pins (not illustrated) to locate the test tubes, microwells, beakers, etc., in particular subsections of the table surface. A vortexing (mixing) table that moves in an orbital pattern can be mounted under tray 12. A full description now follows.

In many instances, it is necessary to mix the reagents after performing a series of pipettings. It is further necessary to mix at a precise interval and duration in relation to previous mixings and pipettings. A third requirement is that the mixing table return to the same X, Y coordinates that is started from.

Figure 11B:
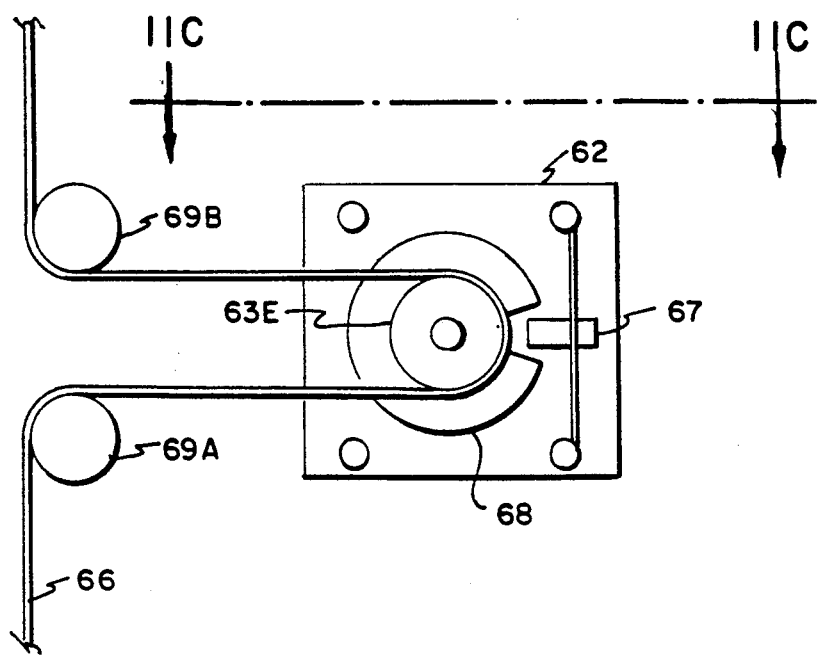
FIG. 11b is a bottom view of the drive motor for the vortexing table showing the timing belt, drive pulley, optical positioning disk and photoswitch.
Figure 11C:
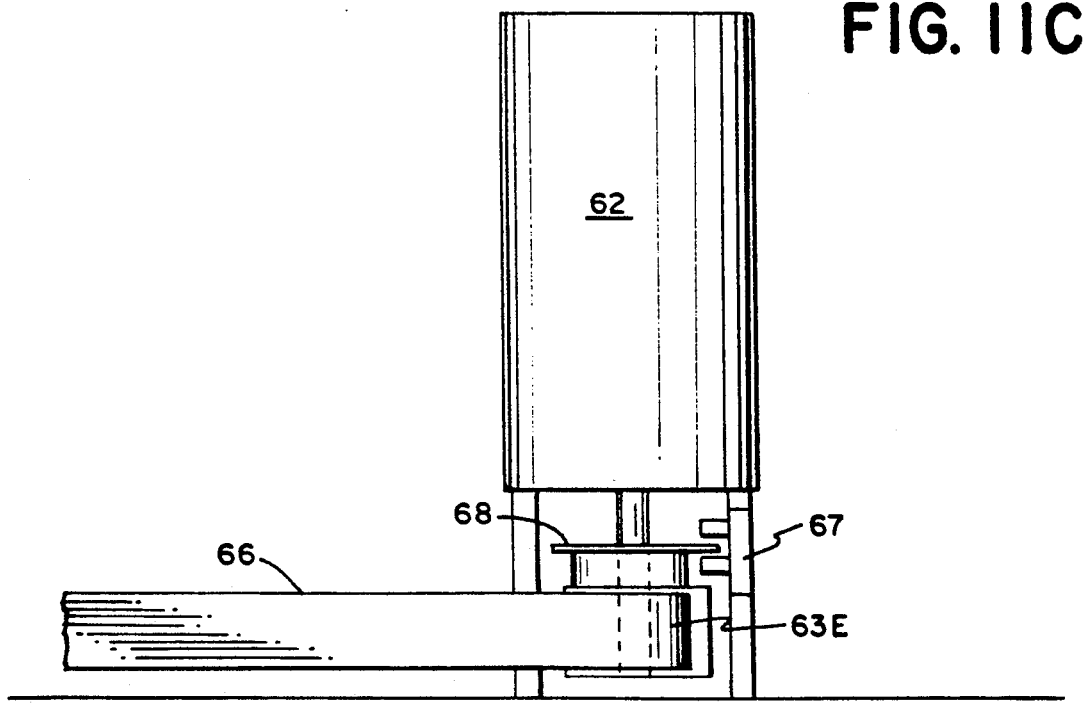
FIG. 11c is a front view along plane 11c–11c of FIG. 11b.

Hereinafter, there is described a vortexing table (mixing table) that is computer controlled as to actuating time, speed and duration, which has a mechanism for maintaining an accurate X, Y position and a photoswitch to enable the vortexing table 61 to return to the precise starting position. Referring to FIGS. 11, 11a, 11b and 11c, ball bearing assemblies 64a, b, c and d are secured to a base 60. Pulleys 63 a, b, c and d are coaxially mounted on shafts 70a, b, c, and d, so as to rotate in bearing assemblies 64a, b, c and d. Offset shafts 71a, b, c and d are fastened to the pulleys 63a, b, c and d and function as a concentric drive. The shafts 71a, b, c and d are inserted into ball bearing assemblies 65a, b, c and d which are fastened to underside of table 61. Timing belt 66 (this timing belt has preferably cogs (not illustrated) to maintain a positive positional relationship) is driven by pulley 63e which is attached to the drive shaft of a motor 62 and guided by idler pulleys 69a and 66b (FIG. 11). As the motor rotates, all the pulleys rotate synchronously by maintaining a positive positional relationship with each other. Offset shafts 71a, b, c and d cause table 61 to oscillate. The starting position is tracked by optical position disk 68 and photoswitch 67 (FIGS. 11b and 11c). When the duration of the mixing cycle is almost completed, the computer (not illustrated) causes motor 62 to slow down and to continue rotating until the photoswitch activates a complete stop at the correct stop position.

Figure 2B:
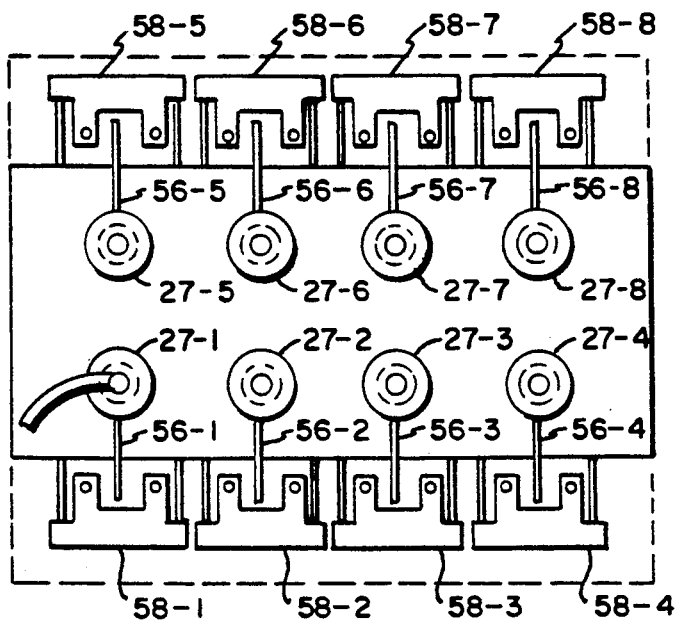
FIG. 2b is a cutaway plan cross-sectional view along plane 2b—2b of the top of the Z-axis assembly showing the relationship between the photocell switches, the flags and the racks.

Carriage 14 carries a number of probes 27 which, in this described and preferred embodiment, are shown arranged in two rows of four probes each. Probes 27-1 to 27-8 (FIG. 2b) are independently movable in the Z-axis directions by separate, stacked drive units, to be described further below. Overhead frame assembly 10 is supported rigidly above tray 12 by vertical supports 16. Chassis 17 houses the electronics and power supply for driving the subframe, carriage, and probe moving mechanisms (preferably stepper motors) shown schematically connected thereto by cables 18a, 18b and 18c, as shown in FIG. 1.

As shown in FIG. 1, frame assembly 10 includes two helical screw shafts 10e and 10f, each disposed adjacent and in parallel with one of the guide shafts 10c and 10d, respectively. The screw shafts 10e and 10f are rotatably mounted inside frame 10a, 10b, and the guide shafts 10c, 10d are rigidly mounted inside frames 10a, 10b. Two stepper drive motors X1 and X2 are mounted on the side of frame support 10a for rotating screw shafts 10e and 10f, respectively. The motors X1 and X2 have independent drives, but are synchronized by their respective home position limit switches (not illustrated) and kept in sync thereafter by the computer. Subframe roller sections 13a and 13b have conventional helix nuts 19a and 19b which are respectively threadably engaged with the threads of X-axis screw shafts 10e and 10f, for driving the roller sections 13a and 13b in the X-axis direction, in accordance with the rotation of the shafts 10e and 10f by stepper drive motors X1 and X2.

Subframe assembly 13 has one helical screw shaft 13e disposed between the Y-axis guide shafts 13c and 13d. Stepper motor drive Y1 is mounted through the rear side of roller section 13b for rotating screw shaft 13e.

Carriage 14 has a conventional helix nut 20 (FIG. 3a) engaged with the threads of the Y-axis screw shaft 13e for driving the carriage 14 in the Y-axis direction upon rotation of the shaft 13e by stepper drive motor Y1.

The construction of the roller sections 13a and 13b, rolling on guide shafts 10c and 10d, is shown in greater detail in FIGS. 5, 5a and 5b in front, side and plan views, respectively. Both roller sections are similarly constructed, so only one section is described in detail herein. The front wall of roller section 13a supports the ends of guide shafts 13c and 13d and screw shaft 13e. The ends of guide shafts 13c and 13d are tensioned by flat springs 21a and 21b (see FIG. 1), which are pressed between the front wall of roller section 13a and end caps 22a and 22b. Translation rollers 24a and 24c are freely rotatable on the ends of shafts 13c and 13d as they roll on top of guide shaft 10c when screw shaft 10e is rotated to move roller section 13a by means of helix nut 19a. They are maintained in position on the guide shaft 10c by positioning roller 23a which is oriented perpendicular to translation rollers 24a and 24c and presses against the side of guide shaft 10c through a rectangular opening 23c in the front wall of roller section 13a, under the biasing force exerted by the flat springs 21a and 21b. A further spring biased positioning roller 26A can optionally be provided, as shown in dotted lines in FIG. 5 and solid lines in FIG. 5b. This roller 26A is rotatable on support shaft 28E(F) which forms part of a lever pivotable at 28I(J) on the wall of roller section 13A(B). A spring 28G(H) is provided to bias roller 26A from underneath against shaft 10c. The axial ends of shafts 13c and 13d are not rigidly fixed to roller section wall 13a, so that they are allowed a slight rotation (flex). The other ends of shafts 13c and 13d (not illustrated) are rigidly fixed to rear wall of roller section 13b, but the wall itself allows a slight flexibility. This combination allows the four rollers 24a, b, c and d of subframe 13 to "seat" on shafts 10c and 10d, respectively, without requiring machining to exacting tolerances. The effect is somewhat similar to getting a set of table legs to all seat on an uneven floor by introducing a small distance to flex into the table. Roller section 13b does not have flat springs similar to 21a and 21b. The remaining construction of roller section 13b is similar. Thus, roller section 13b has translation rollers 24b and 24d and positioning roller 23b, which is pressed against the side of guide shaft 10d by the tension force of flat springs 21a and 21b, applied at the other roller sections 13a, as described above. Roller sections 13a and 13b may also be provided with spring-biased translation rollers 28e, f on the lower sides of the guide shafts 10c, d and positioning rollers 23a, b on the exterior sides of the guide shafts 10c and 10d for a more positive clamping effect on guide shafts 10c and 10d.

Figure 3:
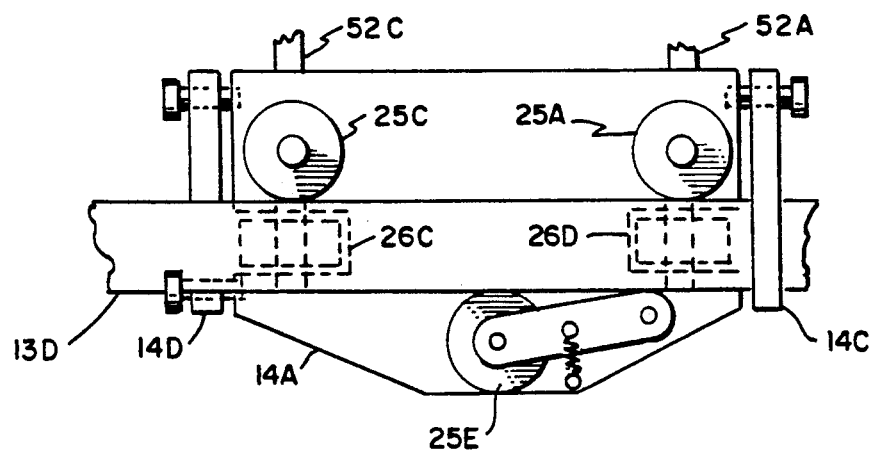
FIG. 3 is an inside side elevational view of one side of the carriage moving along the Y-axis.
Figure 3A:
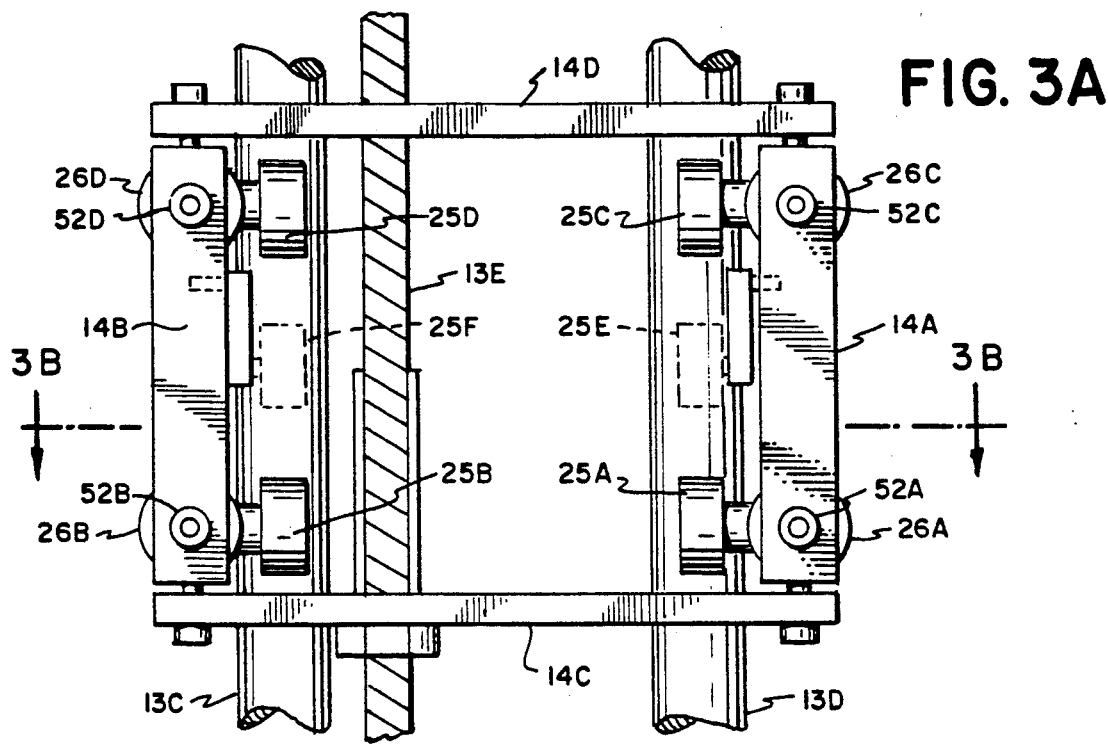
FIG. 3a is a plan view of the carriage of FIG. 3 and its relation to the Y-axis guide shafts.
Figure 3B:
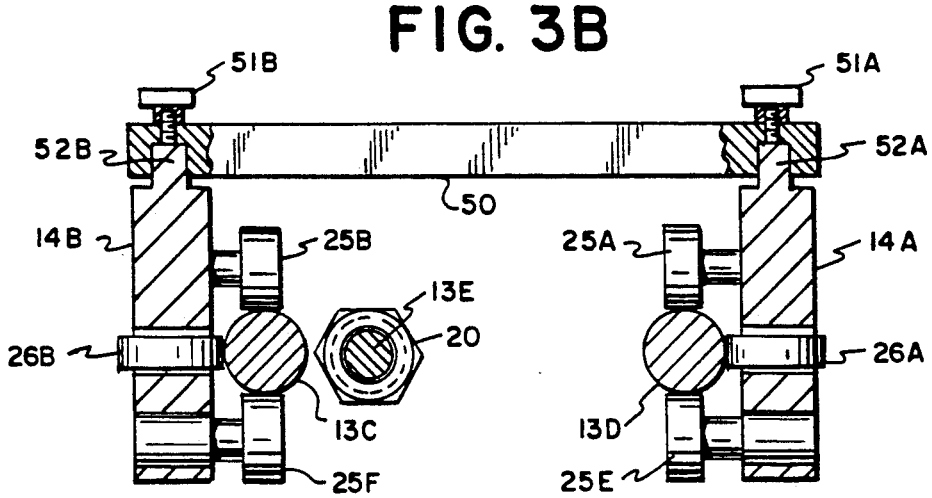
FIG. 3b is a cross-sectional view along plane 3b—3b in FIG. 3a of the carriage shown without the front plate.
Figure 4:
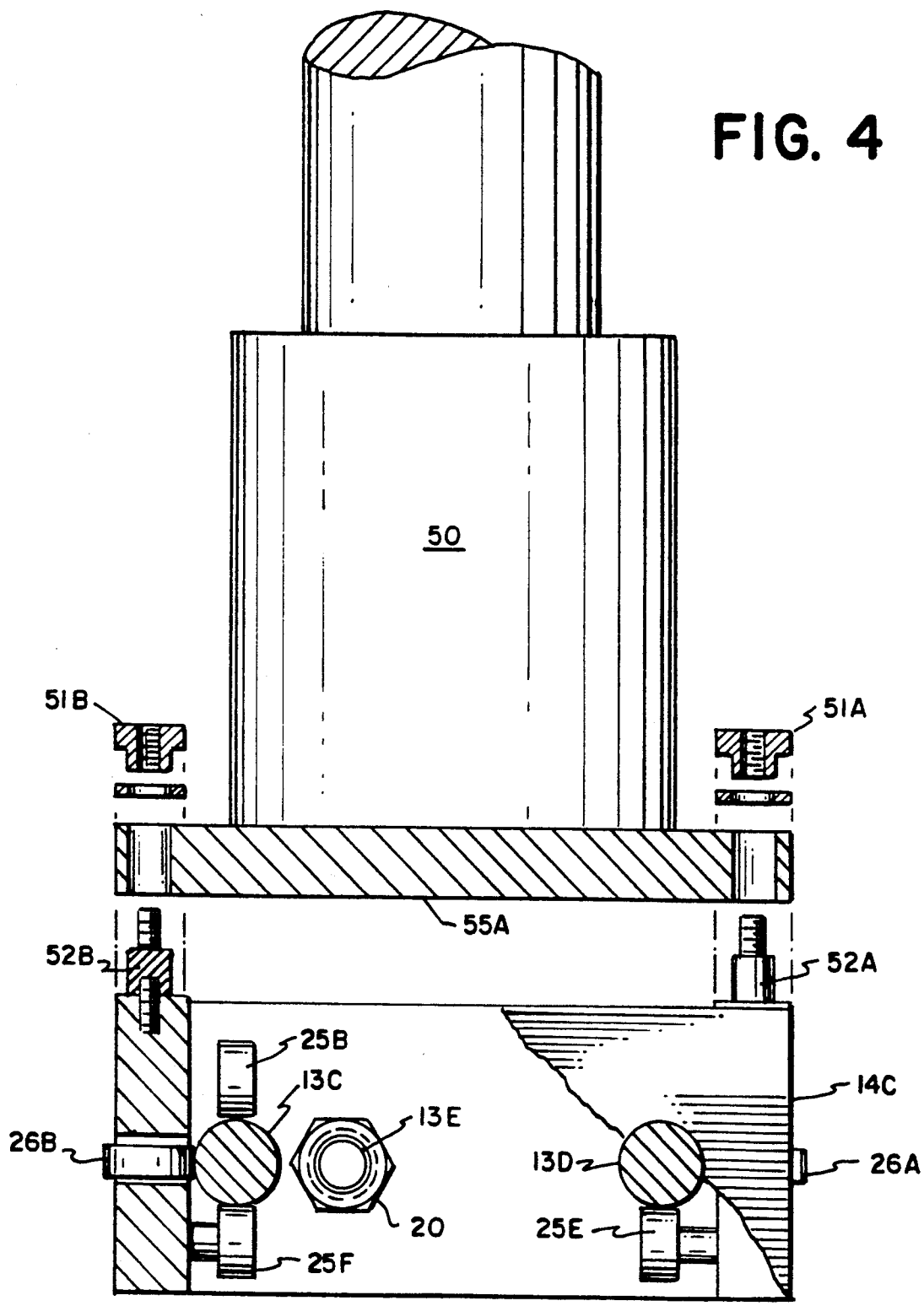
FIG. 4 is an exploded elevational view showing the manner of mounting the Z-axis assembly unit to the carriage.

Carriage 14 has translation rollers 25a, b, c and d rolling on Y-axis guide shafts 13c and 13d, rollers 25e and 25f disposed underneath shafts 13d and 13c, respectively, for clamping action, and lateral positioning rollers 26a and 26c pressing against shaft 13d, with rollers 26b and 26d pressing against shaft 13c in a plane perpendicular to the rolling plane of the translation rollers (FIGS. 3a and 3b).

The helical screw shafts 10e, 10f, 13e of the X-Y positioning frame and subframe assemblies are respectively driven by the stepper motors X1, X2, Y1 to target positions specified by an associated computer (not illustrated) controlling the programmed procedures for the pipetting system. A computer communication link is provided by connectors to casing 17, wherein the electronic controls for the pipetting drive and dispensing mechanisms are housed. The frame and subassembly positioning controls are calibrated by microswitches (not illustrated) provided to mark the home position of the carriage 14 in the X-Y plane. Other home position detectors may, of course, be used, such as optical or magnetic position detectors.

Figure 2C:
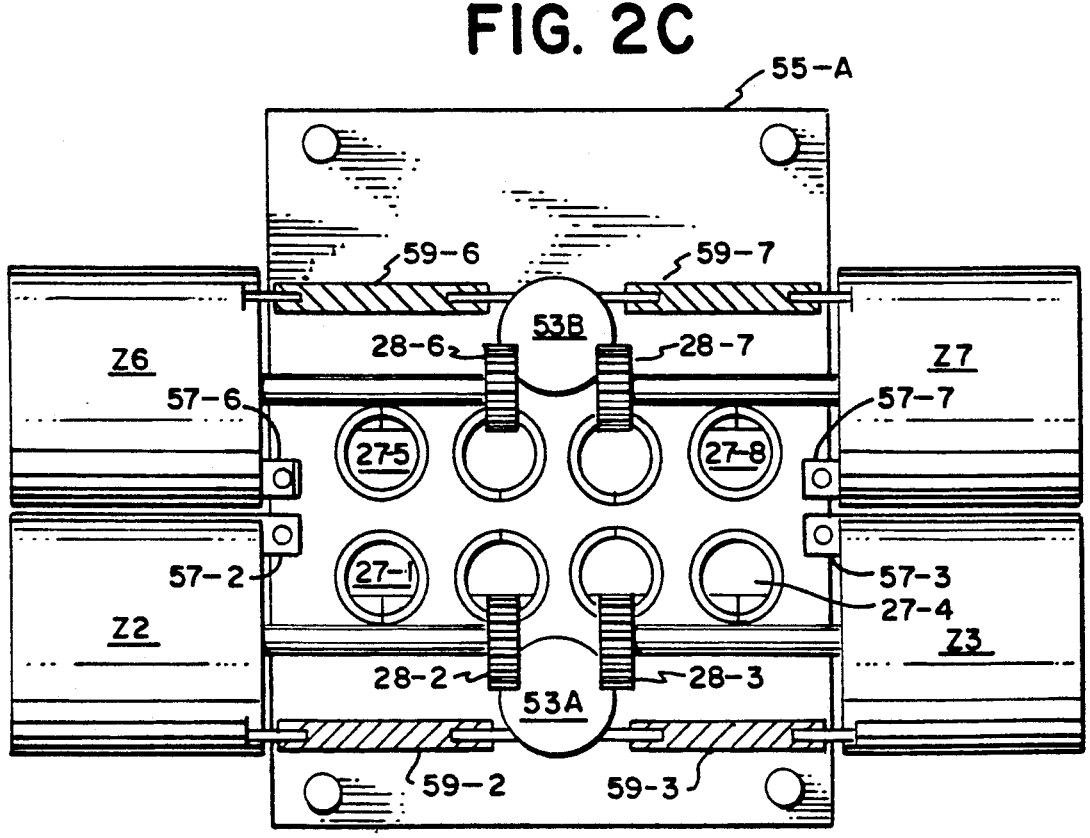
FIG. 2c is a cutaway cross-sectional plan view along plane 2c—2c of the bottom of the Z-axis assembly showing the lower layer of drive motors and their relationship to the racks.
Figure 2D:
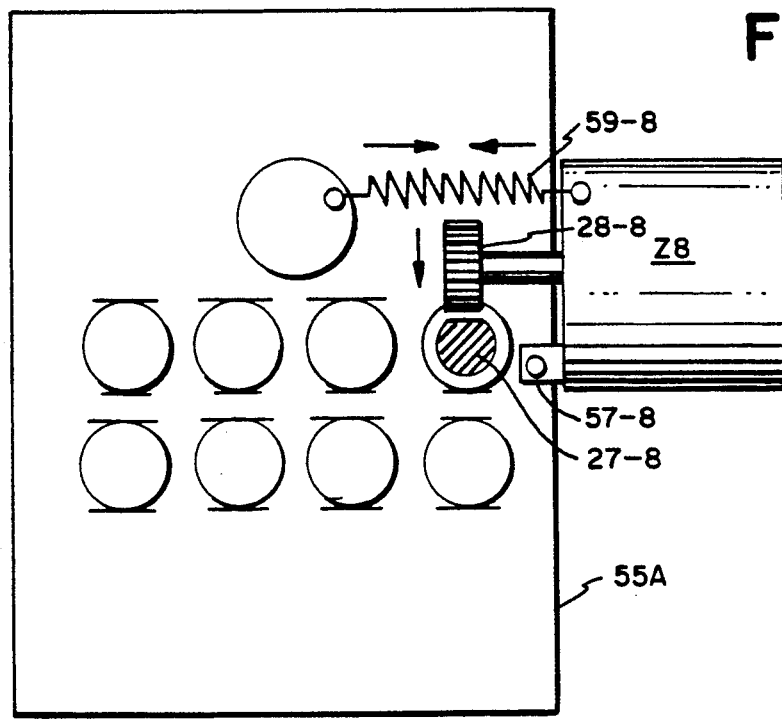
FIG. 2d is a plan schematic view showing the details of the manner of mounting the Z-axis motor in relation to the coacting rack.

Referring now to FIG. 2a, mounting plate 55a and upper support plate 55b, along with support posts 53a and 53b (FIG. 2c) form the frame for supporting the driving mechanisms for the probes in the form of linear racks 27-1, 27-2, 27-3 and 27-4, shown for one row or probes (FIG. 2a) of preferably eight linear racks 27-1 to 27-8 for eight probes. Stepper motors Z1, Z2, Z3 and Z4 drive the linear racks in the Z-axis direction by means of pinion gears 28-1, 28-2, 28-3 and 28-4 fixed to the output shafts of the respective drive motors 21-24. The motors are arranged in a stacked configuration, one above another, on each side of the row of racks, so as to allow the racks and, therefore, the probes, to be spaced close together with a spacing corresponding to the standard configuration for test tubes or microwell arrays, typically 0.75 inch on center. Referring now to FIG. 2d, motor 28 is attached to hinge block 57-8 so that spring 59-8 pulls gear 28-8 against rack 27-8, thereby eliminating backlash as wear occurs. Each one of the Z-axis drive motors is similarly mounted in the carriage 14. The linear racks 27-1, 27-2, 27-3 and 27-4 are slidably in bushings provided through plates 55a and 55b. The Z-axis assembly is shown in FIG. 2c with two rows of four probes in each row. However, additional probes in each row or additional rows may be provided.

Tip holders 36 or non-disposable probes (not illustrated) are attached to ends of racks 27-1 through 27-8. In the preferred configuration, external syringe pumps (not illustrated) are provided for six of the eight probes for pipetting functions (housed in an external unit) and an external two channel peristaltic pump is provided for the other two probes for bulk dispensing or transferring of fluid.

The pumping arrangement for the eight probes are not illustrated in detail. The syringe pump may be used as a standard type of glass syringe. The pump body and syringe are both mounted vertically with the syringe opening facing upward. This end has a luer-look tip which inserts into a bi-directional valve. The valve is computer controlled and allows pumping liquid through the syringe (positive or liquid displacement) or using suction to pull liquid into a disposable tip (air displacement). It can reverse direction, as well. The barrel of the syringe is attached to an arm which is driven up and down by a stepper motor that is directly attached to a lead screw. There is a limit switch at either end to indicate end of travel. The electronics for controlling the action of the pumps are in the power supply 17 for the main transport. The unit is slip mounted on the left side of the main transport and is available in one, two or four channel models. When positive displacement is used a non-disposable tip is used. When using a disposable tip fluid is never drawn so far into the tip, so as to contact the tip holder.

Figure 8:
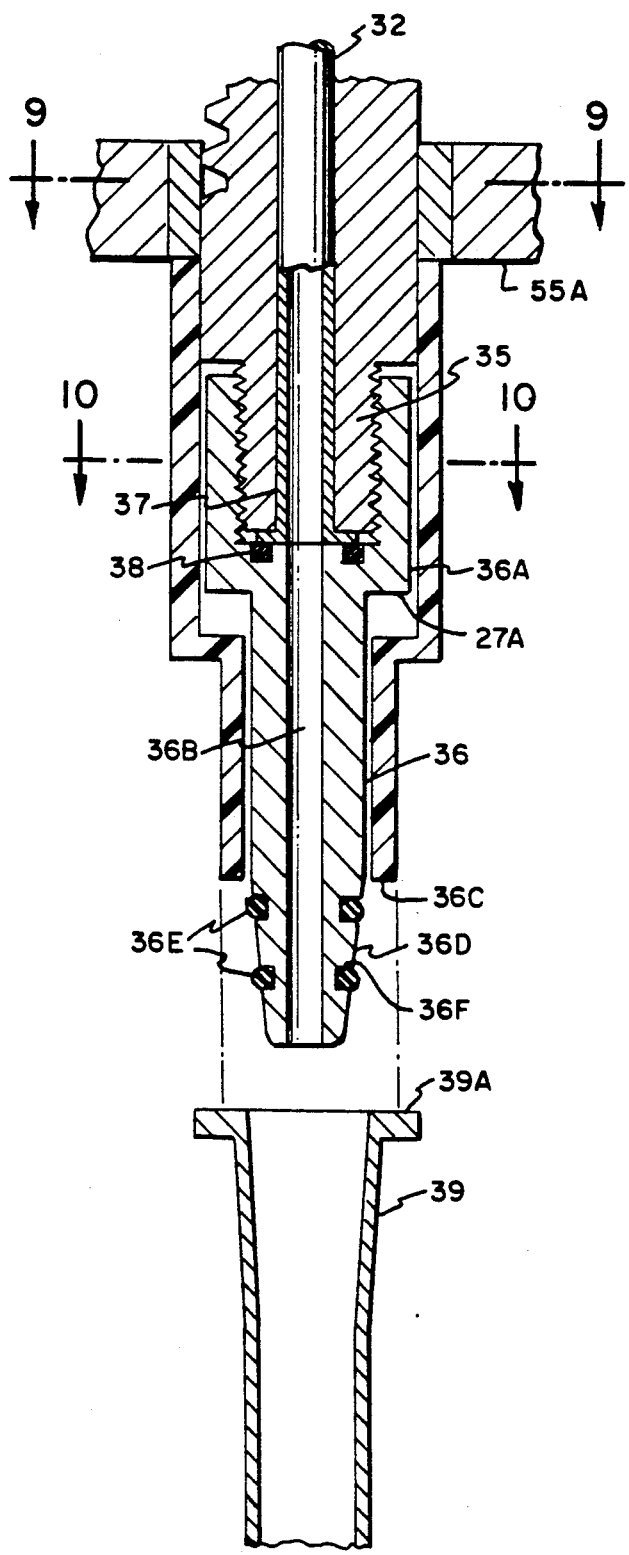
FIG. 8 is a side sectional view of the tip holder shown in a third operative position prior to insertion into a tip.
Figure 9:
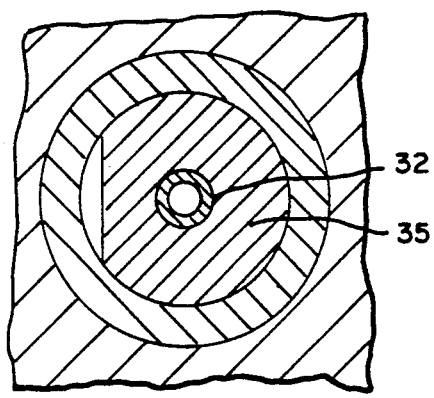
FIG. 9 is a cross-section along plane 9—9 of FIG. 8.
Figure 10:
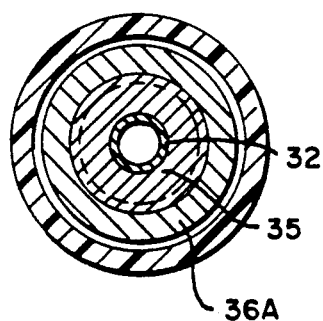
FIG. 10 is a cross-section along plane 10—10 of the probe and tip holder.

The lower ends 35 of the Z-axis racks are threaded for screwing into tip holders 36 shown FIGS. 6–8. Threaded end 35 is screwed into receptacle end 36a of tip holder 36, thereby clamping a teflon top hat 37 and O-ring 38 at its lower portion so as to act as a fluid seal. Passage 36b of tip holder 36 communicates with tubing 32 which is pressed over top hat 37 and passes through hollow rack 27, through tubing guide 80 and exits on side of the frame for connection to external pumps. Lower end of tip holder 36 has a slight taper so that the tip 36 can be smoothly inserted into the similarly tapered upper mouth Y of a disposable tip 39. Shoulder (contact surface) 36c is provided for abutting contrast against the upper face (shoulder) of tip 39 (FIG. 8), so that it is positively positioned and held on tip holder 36. A pair of O-rings 36e are held in the grooves 36f formed on the tapered portion 36c of tip holder 36 so as to provide an air tight seal between tip 39 and tip holder 36 and a friction surface for retaining tip 39 on the tip holder 36.

Pipette tips for the probes may be selected from a range of sizes, such as from 10 to 5000 microliters. The use of syringe pumps allow fluid quantities as small as 10 µl to be dispensed with one percent accuracy and quantities of one microliter with two percent accuracy when the tip ends are touched on or dipped just below the surface of the fluid in the test tubes to break the liquid surface tension.

The improved version of the present invention provides for a faster tip ejection at any XY coordinate. It accomplishes this by moving the probe 35 upward approximately ½ inches past the home position. This causes the probe holder collar 36c to hit the bottom of the Z-axis mounting plate 50 forcing it downward, thus pushing the tip off the tip holder by having the end surface 36d of the collar 36c push against the upper surface 39a of the tip 39. On the 5 ml tip holder, a collar is not necessary because the tip O.D. is larger than the collar 36c O.D. and so that it can be directly contacted by the underside of the Z-axis mounting plate 50. Attachment is accomplished by a synchronized X-Y movement of carriage 14 to the location of fresh tips on base 11, then by downward Z-axis movement of the probes, until the end surface 36d of the tip holders are seated against the upper surfaces or shoulders 39a of the tips 39 (FIG. 6) and ending with a return movement of the probes (FIG. 8). The computer counts the steps required for return movement, and if they are not within a specific range, a warning signal is issued as previously discussed. The associated computer always ejects a tip before picking up a new one and can select which tips are to be replaced or ejected. The computer causes the carriage to be positioned over a box or chute for disposal (or any other preselected disposal portion) and then causes the selected tips to be ejected (all the tips can be ejected simultaneously).

The limit switch of the Applicant's earlier version of the automated pipetting system (see Applicant's co-pending U.S. patent application, Ser. No. 144,576, filed Jan. 14, 1988 now U.S. Pat. No. 5,055,263 issued Oct. 8, 1991) had the drawback that due to the inertial shock of moving in the XY axis, one of the Z axis racks would occasionally move down a few additional steps causing an opening of the associated limit switch, which caused the unit to stop operations. This random nature occasional malfunctioning was due to the fact that stepper motors do not have an equal indent torque for each of their 200 steps. If the motor stopped at a point of its travel at which the torque was very low, the rack would tend to move down a few steps until the stepper motor reached a step with a greater torque. To eliminate this problem, a photo interrupter, i.e., a photocell and LED, was substituted for the mechanical limit switch of the Applicant's earlier version of the automated pipetting system. A flag 56 approximately 0.75 inches in height is attached to the top of the rack 27. When the computer instructs the Z-axis probes to return to home position, the rack 27 moves upward until the top of the flag 56 interrupts the photocell 58 and then travels another 10 steps. When the probe is instructed to move downward, rather than assuming it is exactly at the calibrated home position, it moves downward until the photocell is open and then moves down the indicated number of steps. With this method, if the probe moved downward a few steps during XY travel, it would not affect final Z-axis position. An added benefit of this improvement is that this method allows the probe to move 100 steps past home position enabling tip ejection. The system, in practice, provides a working accuracy to within 0.005 inch over six inches of probe travel.

Other features of the automated pipetting apparatus can include a water bath and temperature controls provided by filling tray or trays on table 12 with water and controlling temperatures as required to maintain the test tube samples thereon at a desired temperature. The trays or table may have different temperature sections. The apparatus may also have a display panel to provide visual confirmation of the status of the programmed procedures being executed by the apparatus. Computer programs for automatically controlling the operation of the pipetting apparatus are used conventionally and are not described herein.

In accordance with the invention, the provision of a frame assembly framing the boundaries of the X-Y pipetting area and the subframe assembly by providing roller sections which roll on the guide shafts disposed at opposite sides of the frame allow the X-Y positioning of the carriage to be carried out accurately and stably, with a minimum of misalignment due to bending or other types of mechanical deflections. The spring tensioning of the guide shafts of the subframe assembly dispenses with the requirement that the two guide shafts must be parallel to a very high degree of precision. The Z-axis motors are arranged in a stacked configuration to allow a close spacing of the probes to fit the spacings of the test tube arrays. The high precision syringe pumps used in the system, coupled with the capability of moving the pipette tips accurately and reliably just below the surface of the liquid, provide the capability to dispense minute quantities of fluid with high accuracy. The use of microswitches and photoswitches and XYZ axes home position calibration ensure precise positioning of the tips relative to the test tube arrays and their fluid levels. The addition of a vortexing table that can accurately return to its starting coordinates and be controlled as to starting time, speed and duration, allow procedures to be carried out automatically, and with more consistent results, that would otherwise require a great deal of manual manipulation. All of these features and advantages achieve a greatly improved functioning of the automated pipetting system over the prior art pipetting system.

SUMMARY OF IMPROVEMENTS (1) The lower manufacturing cost, while maintaining high precision;

(2) The frame of pipetting system is more portable than the prior art systems and can be manufactured in a way that makes dimensional changes simple and inexpensive.

(3) The Z-axis carriage is a modular, detachable and interchangeable unit which makes the XY axes frame or basic unit for a multitude of different applications.

(4) The power supply unit is detachable and can be used in remote locations when necessary.

(5) The syringe pumps can be attached to the side of the XY axes frame and pump liquid through the syringe body.

(6) The tip ejection system is simple, rugged and reliable (7) The Z-axis limit switch is of the optical type and has improved operational characteristics.

(8) The Z-axis motors are spring loaded against the rack to take up backlash.

(9) Two O-rings are used on the tip holders for improved sealing (except on the 5 ml probe holder).

(10) The vortexing table allows complete automation of certain procedures.

Although a preferred embodiment of the invention has been described above, it should be understood that many variations and modifications are possible within the disclosed principles of the present invention. For example, the configuration of the various roller sections may be modified. It is intended that the embodiment described herein, and all such variations and modifications, be included within the scope of the invention, as defined in the appended claims.

What is claimed is:

1. An automated pipetting system for performing programmed pipetting quantitative transfer of fluids between preselected units of an array of test tubes comprising:

a horizontal table for holding test tube arrays;

a substantially rigid overhead frame defining a horizontal X-Y pipetting area, which is spaced vertically above said horizontal table for holding the test tube arrays;

a pair of X-axis guide shafts fixedly mounted and spaced apart in parallel on two opposite sides of said frame;

a pair of X-axis helical screw shafts rotatably mounted in the frame, each disposed adjacent and parallel to a respective one of said X-axis drive means operatively connected to said pair of X-axis screw shafts for driving said X-axis screw shafts synchronously in rotation;

a subframe assembly having a pair of X-axis roller sections, each X-axis roller section of said pair having a support wall provided with a helix engagement portion which threadedly engages one of said X-axis helical screw shafts for moving said subframe assembly along an associated X-axis guide shaft in the X-axis directions in response to rotation of the associated X-axis helical screw shaft;

a pair of Y-axis guide shafts supported on the subframe assembly by being sections connected at its opposite ends to said pair of X-axis roller operatively, said four X-axis shafts being spaced parallel to each other and perpendicular to said pair of Y-axis guide shafts;

a Y-axis helical screw shaft rotatably mounted in said pair of Y-axis roller sections parallel to the two Y-axis guide shafts;

Y-axis driving means operatively connected to said Y-axis helical screw shaft for driving said Y-axis screw shaft in rotation;

a carriage having a pair of Y-axis roller sections rolling on the pair of Y-axis guide shafts, and further having a support wall provided with a helix engagement portion engaging said Y-axis helical screw shaft for moving said carriage in the Y-axis direction in response to rotation of said Y-axis helical screw shaft;

at least one Z-axis modulator removable unit having at least one row of probes said Z-axis modular unit being removably mounted on said carriage for movement in the Z-axis directions by a Z-axis drive means;

said Z-axis drive means being operatively connected to each probe for independently driving respective ones of said probes in the Z-axis direction relative to the test tube array on said table, said Z-axis direction being perpendicular to said X and Y axes directions; and computer control means operatively connected to said X, Y and Z axes drive means.

2. The automated pipetting system according to claim 1, wherein said X, Y and Z axes drive means are computer controlled stepper motors.

3. The automated pipetting system according to claim 2, wherein one of the ends of each one of said pair of Y-axis guide shafts is resiliently mounted in one X-axis roller section by means of a plate spring disposed between said support wall of said X-axis roller section and a retaining portion secured to said one end of the Y-axis guide shaft.

4. The automated pipetting system according to claim 3, wherein each X-axis roller section includes a first pair of rollers rotatably mounted on said support wall for riding on top of one of said X-axis guide shafts.

5. The automated pipetting system according to claim 4, wherein each X-axis roller section further includes a spring biased second roller rotatably mounted on said support wall which abuts against said associated X-axis guide shaft from below, and on the opposite side of the associated X-axis guide shaft, on which said first pair of rollers ride.

6. The automated pipetting system according to claim 4, wherein at least one of said X-axis roller sections include, a third roller which is rotatably supported on the exterior side of said support wall, said support wall having an opening, said third roller abutting against the associated X-axis guide shaft through said opening and being substantially perpendicularly disposed relative to said first and second rollers.

7. The automated pipetting system according to claim 1, wherein said Z-axis modular removable unit includes a mounting plate having at least a pair of openings, said carriage having at least one pair of threaded locator pins which extend through said pair of openings when said Z-axis unit is mounted on said carriage, and a pair of threaded nuts adapted to be threadably mounted on said locator pins to rapidly mount said Z-axis unit on said mounting plate.

8. The automated pipetting system according to claim 7, wherein said Z-axis carriage includes a pair of side walls, each side wall has a pair of first rollers rotatably mounted thereon which are adapted to roll over an associated one of said pair of Y-axis guide shafts.

9. The automated pipetting system according to claim 8, wherein said Z-axis carriage further includes a spring biased second roller rotatably mounted on each one of said side walls which abuts against said associated Y-axis guide shaft from below, and on the opposite side thereof, on which said first pair of rollers ride.

10. The automated pipetting system according to claim 8, wherein said Z-axis carriage further includes a pair of third rollers which are rotatably mounted in an associated one of said pair of side walls, said pair of third rollers abutting against an associated one of said pair of Y-axis guide shafts and being substantially perpendicularly disposed relative to said first and second rollers.

11. The automated pipetting system according to claim 1, wherein said Z-axis modular unit includes at least one Z-axis probe having a linear rack which is independently movably mounted along the Z-axis in said modular unit; and a stepper motor having a pinion drive gear operatively mounted in said Z-axis modular unit, said pinion gear having means for meshing with said linear rack for reciprocally moving said probe along the Z-axis in accordance with the signals transmitted to said stepper motor by said computer control means.

12. The automated pipetting system according to claim 1, wherein said Z-axis modular unit includes two parallel rows of Z-axis probes and four probes being disposed in each row, the linear rack of each probe being having means for meshingly engaging by the pinion drive gear of an operatively associated stepper motor, the stepper motors for each row of four probes being operatively mounted in a stacked arrangement in said unit.

13. The automated pipetting system according to claim 12, wherein said stepper motor is pivotally mounted in said modular unit, and spring biasing means connected to said stepper motor for urging said pinion gear into meshing engagement with said linear rack.

14. The automated pipetting system according to claim 12, including a photoelectric sensing means operatively mounted in said modular unit and associated with each linear rack, so as to transmit a signal to said computer control means when said rack reaches a predetermined position.

15. The automated pipetting system according to claim 11, wherein each probe includes a tip holder at the lower end of said linear rack for holding changeable tips thereon, said linear rack being hollow, and tubing extending through said linear rack for external connection to a pump; and said tip holder having a lower end of frustoconical shape, at least one annular groove on said lower end of said tip holder, and an O-ring mounted in said annular groove.

16. The automated pipetting system according to claim 15, wherein said lower end of frusto-conical shape has a pair of concentric annular grooves, a pair of O-rings mounted in said pair of grooves, said O-rings frictionally engaging the interior surface of a tip when the associated probe is lowered a predetermined distance along the Z-axis by action of said computer control means which drives said linear rack via the associated stepper motor, whereby said pair of O-rings are disengaged from the interior surface of said tip when the associated probe is raised a predetermined distance.

17. The automated pipetting system according to claim 1, wherein said horizontal table for holding the test tube arrays includes vibrating means operatively connected thereto for vibrating the test tubes, said vibrating means also being operatively connected to said computer control means.

18. The automated pipetting system according to claim 17, wherein said vibrating means includes a motor which is connected to said computer control means, said motor having a drive pulley, a plurality of idler pulleys being rotatably mounted in a base which is disposed underneath said horizontal table, each pulley having an axial first support shaft which is rotatable in said base and is biased toward the pulley, and a second shaft parallel to said first shaft which is rotatably, but eccentrically mounted therein and which is rotatable in said horizontal table, and a belt drivingly engaging said drive pulley and said plurality of idler pulleys.

19. The automated pipetting system according to claim 18, wherein said belt is a timing belt which has uniformly spaced caps for positively engaging said drive pulley and said plurality of idler pulleys, and stop means operatively connected to said drive motor where stopping the movement of said drive pulley at a preselected location.

20. The automated pipetting system according to claim 13, wherein said stop means includes a photocell operatively mounted adjacent to one of said pulleys, and connected to said motor, and photocell circuit interrupting means mounted on said one pulley for detecting when said pulley has reached a preselected stop position.

* * * * *